US005693585A

United States Patent [19]

Benazzi et al.

[11] Patent Number: 5,693,585
[45] Date of Patent: Dec. 2, 1997

[54] ALIPHATIC ALKYLATION CATALYST COMPRISING AN ACTIVE PHASE CONTAINING A CUPROUS COMPOUND ON A SUPPORT

[75] Inventors: Eric Benazzi, Montesson; Yves Chauvin, Le Pecq; André Hirschauer, Montesson; Nathalie Ferrer, Chatou; Hélène Olivier, Rueil Malmaison; Jean-Yves Bernhard, Mennecy, all of France

[73] Assignee: Institut Francais du Petrole, Rueil Malmaison, France

[21] Appl. No.: 664,538

[22] Filed: Jun. 17, 1996

[30] Foreign Application Priority Data

Jun. 15, 1995 [FR] France ........................... 95 07270
Jun. 15, 1995 [FR] France ........................... 95 07271

[51] Int. Cl.$^6$ .................... B01J 27/125; B01J 31/00; B01J 27/25; B01J 27/122
[52] U.S. Cl. .................... 502/231; 502/150; 502/164; 502/165; 502/167; 502/169; 502/170; 502/171; 502/201; 502/218; 502/225; 502/231
[58] Field of Search .................... 502/150, 164, 502/165, 167, 169, 170, 171, 201, 218, 225, 231

[56] References Cited

U.S. PATENT DOCUMENTS

| 2,337,014 | 12/1943 | Crawford et al. | 260/683.4 |
| 5,276,242 | 1/1994 | Wu | 585/709 |
| 5,406,018 | 4/1995 | Sherman | 585/729 |

FOREIGN PATENT DOCUMENTS

| 0 443 167 | 8/1991 | European Pat. Off. . |
| 0 553 009 | 7/1993 | European Pat. Off. . |
| 553009 | 7/1993 | European Pat. Off. . |
| 2 161 904 | 7/1973 | France . |
| 2 626 572 | 8/1989 | France . |

*Primary Examiner*—Glenn A. Caldarola
*Assistant Examiner*—Thuan D. Dang
*Attorney, Agent, or Firm*—Millen, White, Zelano, & Branigan, P.C.

[57] ABSTRACT

A catalyst containing a porous organic or mineral support and at least one active phase having at least one aluminum halide, at least one compound selected for quaternary ammonium halides and amine hydrohalides, and at least one cuprous compound, the support having been impregnated with the active phase, the catalyst essentially constituted by particles with an average diameter in the range 0.1 µm to 150 µm, and the support, before impregnation with the active phase, has a total pore volume in the range 0.1 cm$^3$/g and 6 cm$^3$/g.

18 Claims, No Drawings

ALIPHATIC ALKYLATION CATALYST COMPRISING AN ACTIVE PHASE CONTAINING A CUPROUS COMPOUND ON A SUPPORT

The present invention concerns a catalyst comprising a porous organic or mineral support and at least one active phase constituted by at least one aluminum halide, at least one amine hydrohalide and/or at least one quaternary ammonium halide and at least one cuprous, Cu(I), compound. The invention also concerns the use of the catalyst for aliphatic alkylation, i.e., catalytic alkylation of isobutane and/or isopentane by means of at least one olefin containing 2 to 6 carbon atoms per molecule (i.e., a $C_2$–$C_6$ olefin), to obtain paraffinic compounds with a high degree of branching and a high octane number.

BACKGROUND OF THE INVENTION

A large number of liquid or solid acid catalysts are known for carrying out the aliphatic alkylation of isoparaffin(s) such as isobutane or isopentane using at least one olefin such as propylene, 1- and 2-butene and isobutene. Concentrated sulphuric acid and hydrofluoric acid, alone or mixed with Lewis acids such as boron trifluoride, are the most frequently used industrial catalysts. These processes suffer from major drawbacks: hydrofluoric acid due to its toxicity and high volatility; and sulphuric acid due to a high consumption of catalyst requiring expensive reprocessing. For this reason, the use of catalysts which are solid or supported on solids such as aluminosilicates or metal oxides, such as zirconia treated with sulphuric acid, has been recommended.

European patent application EP-A-0 553 009 describes the use of liquid ionic complexes on a porous organic or mineral support to catalyze aliphatic alkylation. Such complexes are formed by aluminum halides with certain quaternary ammonium halides or with certain amine hydrohalides. Such complexes, also known as "molten salts", have been described by C. H. Hussey in *Advances in Molten Salts Chemistry*, vol. 5, p 185, Elsevier, N.Y., 1985, and by C. A. Angell and J. W. Shuppert in J. Phys. Chem. 84, 538, 1980, and form the subject matter of French patents FR-A-2 626 572 and FR-A-2 692 888.

SUMMARY OF THE INVENTION

The present invention concerns a catalyst containing a porous organic or mineral support, preferably silica, and at least one active phase containing at least one aluminum halide, at least one quaternary ammonium halide and/or at least one amine hydrohalide, i.e., at least one compound selected from amine hydrohalides and quaternary ammonium halides, and at least one cuprous compound, the support having been impregnated with the active phase, the catalyst being such that it is essentially constituted by particles with an average diameter in the range 0.1 µm to 150 µm, preferably in the range 5 µm to 110 µm, more preferably in the range 5 µm to 80 µm, and the support, before impregnation with the active phase, has a total pore volume in the range 0.1 cm³/g and 6 cm³/g, preferably in the range 0.2 cm³/g to 5.5 cm³/g, more preferably in the range 0.3 cm³/g to 5 cm³/g.

Surprisingly, the catalyst of the present invention leads to improved catalytic performances compared with those described in European patent application EP-A-0 553 009. We have unexpectedly discovered that the addition of copper (I) compounds, in particular cuprous halides, to the ionic complexes described in the cited patent application improves the selectivity and stability of the catalyst, preventing the introduction of additional protons to reactivate the catalyst and reducing the chlorine content of the alkylates which are the reaction products.

European patent application EP-A-0709356 describes a catalytic composition resulting from a mixture of at least one aluminum halide, at least one quaternary ammonium halide and/or at least one amine hydrohalide and at least one cuprous compound, preferably a halide. The cited application also describes a process for alkylation of isoparaffins by olefins using this composition. The present application thus describes a catalyst containing the catalytic composition described in European patent application EP-A-0 709 356, on a support.

The catalyst of the present invention includes a porous organic or mineral support, preferably silica, and at least one active phase containing at least one aluminum halide, at least one amine hydrohalide, preferably an amine hydrochloride or hydrobromide, and/or at least one quaternary ammonium halide, and at least one cuprous Cu(I) compound. The support is impregnated by at least one active phase whose composition has been described above. The active phase is an ionic complex which is not miscible with the hydrocarbon phase, commonly known as a molten salt. It can be obtained at ambient temperature, but also at a higher temperature, preferably less than 150° C., more preferably less than 100° C. In all cases, it is liquid when impregnated into the support.

The aluminum halide which is of particular use in the present invention is selected from the group formed by aluminum trifluorides, trichlorides and tribromides such as $AlCl_3$ or $AlBr_3$. It can be used pure or as a mixture, for example, in various proportions from 99% of one of the halides to 99% of the other in the case of a mixture of two aluminum halides. $AlCl_3$ can thus be mixed with $AlBr_3$, for example.

The quaternary ammonium halide for use in the present invention is selected from the group formed by quaternary ammonium salts, which may be acyclic or form part of a cycle, which have the following general formulae:

$$R^1R^2R^3R^4N^+\ X^- \qquad (I)$$

$$R^1R^2N^+=CR^3R^{4+}\ X^- \qquad (II)$$

(III)

(IV)

where $R^1$, $R^2$, $R^3$, $R^4$ and $R^5$ which may be identical or different, each represent hydrocarbon residues which generally contain 1 to 12 carbon atoms, for example alkyl, cycloalkyl, aryl or aralkyl. $R^5$ may also represent hydrogen or substituted hydrocarbon residues containing other atoms such as nitrogen, for example.

Radicals such as $R^6$ may unite two of the above molecules as, for example in $R^1R^2N^+=CR^3-R^6-CR^3=N^+R^1R^2$ $(X^-)_2$. $R^6$ may be an alkylene residue or a phenylene residue.

The cyclic part of the compounds III and IV are constituted by 4 to 10 atoms, preferably 5 or 6 atoms which, in addition to the nitrogen of the quaternary ammonium, may contain carbon atoms or other nitrogen atoms, generally 1 or 2.

Examples of the $R^1$, $R^2$, $R^3$, $R^4$ or $R^5$ groups are methyl, ethyl, propyl, isopropyl, butyl, secondary butyl, tertiary butyl, amyl, methylene, ethylidene, phenyl or benzyl radicals; $R^6$ may be a methylene, ethylene, propylene or phenylene group.

In these formulae, X represents a halide ion, for example a bromide or chloride ion.

Particular examples of ammonium salts for use in the invention are imidazolium and pyridinium salts such as N-butylpyridinium chloride, ethylpyridinium bromide, 1-butyl-3-methylimidazolium chloride, diethylpyrazolium chloride, and 1-ethyl-3-methyl-imidazolium chloride.

The amine hydrohalide for use in the invention, preferably the amine hydrochloride or hydrobromide, preferably contains one mole of hydrohalic acid, preferably hydrochloric or hydrobromic acid, per mole of amine, but can also contain two moles of acid per mole of amine. Mixtures of hydrohalides to one or two moles of hydrohalic acid can also be used. The hydrohalide derives from an acyclic amine or diamine or an amine forming part of a cycle which can contain one or more nitrogen atoms and has one of the following general formulae:

  (I)

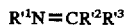  (II)

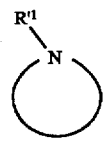  (III)

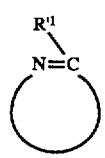  (IV)

where $R'^1$, $R'^2$, $R'^3$, which may be identical or different, represent hydrocarbon residues which generally contain 1 to 12 carbon atoms, for example alkyl, cycloalkyl, aryl, or aralkyl. One of the $R'^1$, $R'^2$, $R'^3$ substituents may be hydrogen. The cyclic part of the compounds III and IV generally constitute 4 to 10 atoms, preferably 5 or 6 atoms and, in addition to one or more nitrogen atoms, may contain carbon atoms bonded by single or double bonds. The cyclic part of the compounds III and IV may be condensed with other cycles and may carry substituents as defined above, amine functions, fluorine atoms, chlorine atoms or bromine atoms.

Examples of $R'^1$, $R'^2$, $R'^3$ groups are methyl, ethyl, propyl, isopropyl, butyl, sec-butyl, amyl, methylene, ethylidene, phenyl and benzyl radicals. The cyclic part of the compounds such as IV are represented by pyridines, imidazoles, triazines, pyrazoles, pyrimidines and triazoles.

The hydrohalide is preferably selected from the group formed by pyridine hydrochlorides or hydrobromides, 2-, 3- or 4-picolines, lutidines, 2-ethylpyridine, 3-isopropylpyridine, 2- or 4-chloropyridine, N,N-dimethyl-4-aminopyridine, N-methylimidazole, N-butylimidazole, piperidine, and N-methylimidazoline.

An essential feature of the invention is the presence of copper (I) in the active phase on the support.

The copper (I) compound which can be used in the invention is generally selected from the group formed by cuprous halides, cuprous acetate, cuprous sulphate, cuprous nitrate and cuprous perchlorate. Preferably, the compound is a cuprous halide, which avoids introducing additional ions into the reaction medium used to form the active phase. The most preferred copper halide is selected from the group formed by cuprous chloride and cuprous bromide.

The components of the active phase as defined above are preferably used in molar ratios [aluminum halide:quaternary ammonium halide and/or amine hydrohalide] in the range 1.1:1 to 3.5:1, preferably in the range 2:1 to 3:1, and (aluminum halide:cuprous halide) in the range 1:0.1 to 1:1, preferably in the range 1:0.2 to 1:0.5.

The compounds contained in the composition of the active phase of the invention which is then impregnated into the support can be mixed in any order at a temperature in the range −20° C. to +80° C. The mixture can be formed by simple contact followed by stirring to form a liquid or suspension which can be processed. When the cuprous compound is a cuprous halide, the operation can advantageously be carried out by mixing only about one third of the aluminum halide with the quaternary ammonium halide and/or amine hydrohalide, the compound obtained then easily dissolving the cuprous compounds, then adding the two remaining thirds of the aluminum halide. This avoids the need to use basic solvents to aid dissolution of the cuprous compound. In this way, a homogeneous preparation is obtained which is easy to process and which impregnates the support easily.

When silica is used as the support, it can contain impurities such as oxides, alkalis, alkaline-earths, aluminum compounds or any other known impurity, the total quantity of these impurities generally not exceeding 2% by weight with respect to the silica.

The organic or mineral support, preferably silica, is generally such that, before impregnation by the acid phase, the specific surface area is in the range 0.1 m$^2$/g to 1500 m$^2$/g, and its total pore volume is in the range 0.1 cm$^3$/g to 6 cm$^3$/g, preferably in the range 0.2 cm$^3$/g to 5.5 cm$^3$/g, and more preferably in the range 0.3 cm$^3$/g to 5 cm$^3$/g. Further, it is generally mainly constituted by particles with an average diameter in the range 0.1 μm to 150 μm, preferably in the range 5 μm to 110 μm, and more preferably in the range 5 μm to 110 μm.

The active phase (also termed the "molten salt") generally occupies 80% to 100% of the total pore volume of the support, preferably 90% to 100% of the pore volume.

The weight content of the active phase of the catalyst is in the range 1% to 48%, preferably in the range 10% to 48% by weight.

The process for the preparation of the catalyst of the invention generally includes at least two steps. In a first step, the porous organic or mineral support is calcined at a temperature of more than 50° C., preferably more than 80° C., and more preferably in the range 150° C. to 600° C., for example at about 500° C. The duration of the calcining step is normally in the range 10 minutes to 50 hours, preferably in the range 15 minutes to 25 hours. Calcining is generally carried out in the presence of dry air or a dry air/nitrogen mixture with a flow rate in the range 0.001 l/h/g to 10 l/h/g, preferably in the range 0.1 l/h/g to 5 l/h/g. The second step consists of impregnating the calcined support with the active phase. This second step can be effected using any technique known to the skilled person. Generally, an additional step of preparing the active phase prior to the impregnation step is added to this preparation process.

The catalyst of the present invention is used in a process which can effect alkylation of an isoparaffin by olefins under optimal conditions. In particular, since the reaction is characterized by high exothermicity (about 83.6 kJ/mol of butene transformed when the olefin is butene and the isoparaffin is isobutane), the use of the catalyst of the present invention means that good homogeneity of temperature and reactant concentration is obtained.

In the isoparaffin alkylation process using the catalyst of the present invention, the operating conditions, in particular the temperature and pressure, are generally selected such that the mixture constituted by the isoparaffin, olefin(s) and the reaction products is liquid. Further, it is important that the catalyst is immersed in the liquid to ensure good liquid-solid contact.

The catalyst of the invention is advantageously used in a reaction zone for the alkylation of isobutane and/or isopentane with at least one olefin containing 2 to 6 carbon atoms per molecule, in the liquid phase and mixed with the isoparaffin and/or mixture of isoparaffins. The catalyst of the invention can be used in an expanded bed, in a near perfectly stirred reaction zone or in a circulating bed, and preferably it is used in a process which uses a continuous liquid phase, the catalyst being used in the form of a suspension in the two preferred implementations described below.

A first preferred implementation for the catalyst of the present invention uses a near perfectly mixed reaction zone, i.e., a perfect mixture or a near perfect mixture (stirred or Grignard tank) using at least one stirring means, for example at least one screw, to obtain sufficient stirring of the catalyst suspended in the liquid hydrocarbon phase, which latter generally comprises the isoparaffin (isobutane and/or isopentane), at least one olefin, possibly at least one inert diluent (for example propane or normal-butane) and the alkylation reaction products. The feed to be conveyed, constituted by isobutane and/or isopentane and at least one olefin, can for example be introduced as a liquid at at least one point into the liquid hydrocarbon phase present in the reaction zone.

A second preferred implementation for the catalyst of the present invention in suspension in a hydrocarbon phase is a co-current mobile bed, i.e., a circulating bed. In this implementation, the catalyst in suspension in the liquid hydrocarbon phase, generally comprising the isoparaffin (isobutane and/or isopentane), at least one olefin, possibly an inert diluent (for example propane or normal-butane) and the alkylation reaction products, circulates from bottom to top in the reaction zone. The ensemble constituted by the catalyst suspended in the hydrocarbon phase then circulates through at least one heat exchanger and at least one pump, before being reintroduced into the reaction zone inlet. The feed to be converted, constituted by isobutane and/or isopentane and at least one olefin, is introduced either as a liquid or a gas at at least one point in the reaction zone.

In the two implementations described above, the isoparaffin (isobutane and/or isopentane) which is unconverted or has been introduced in excess with respect to the reaction stoichiometry is generally recycled after separation from the alkylate, either by direct introduction into the reaction zone, or by mixing with the feed to be converted.

The isoparaffin-olefin mixture is generally introduced into the reaction zone at an hourly space velocity, expressed as the weight of olefin introduced per unit weight of catalyst per hour (wwh), in the range 0.001 $h^{-1}$ to 10 $h^{-1}$, preferably in the range 0.002 $h^{-1}$ to 2 $h^{-1}$. The mixture can also be formed inside the reaction zone. In all cases, the mixture produced is in the reaction zone under pressure and temperature conditions which ensure that the hydrocarbon mixture remains in the liquid state on the catalyst.

The reaction temperature is generally in the range −40° C. to +80° C., preferably in the range −20° C. to +25° C. The pressure in the reaction zone is generally sufficient to maintain the hydrocarbons in the liquid state in the zone.

In order to limit secondary reactions, an excess of isoparaffin with respect to olefin is generally used. As an example, when alkylating isobutane with butene, the isobutane can be introduced pure into the feed or as a mixture of butanes containing, for example, at least 40% of isobutane. Further, the butene can be introduced pure or as a mixture of butene isomers. In all cases, the isobutane/butene molar ratio in the feed is generally in the range 1 to 100, preferably in the range 3 to 50 and more preferably in the range 5 to 15.

When the nature of the catalyst and the reaction conditions are correctly selected (in particular the temperature), the catalyst of the invention can produce alkylation products of at least one isoparaffin by at least one olefin which are important as engine fuels and petrol constituents and which contain, for example, at least 60 mole % of paraffins containing 8 carbon atoms per molecule and less than 1 mole % of unsaturated compounds, the paraffins containing 8 carbon atoms per molecule containing 70 to 98 mole % of trimethylpentanes.

A further advantage of the catalyst of the present invention is the possibility of alkylating isobutane at low temperatures with mixtures of olefins containing 2 to 6 carbon atoms per molecule, where the proportion of olefins containing more than 4 carbon atoms per molecule is very high.

The following examples illustrate the invention without limiting its scope.

Example 1

Preparation of catalyst 1, in accordance with the invention 13.7 g of 1-butyl-3-methylimidazolium and 20 ml of heptane were successively introduced into a glass flask provided with a magnetic stirrer, purged of air and moisture and held at 10° C., followed by portionwise introduction of 8.5 g of freshly sublimed aluminum chloride. A liquid composition was obtained which was introduced into a further flask containing 4.7 g of anhydrous cuprous chloride which slowly dissolved in the ionic mixture. 14.5 g of aluminum chloride was added portionwise to this solution and was slowly dissolved in the liquid composition.

16 g of silica with a specific surface area of 395 m²/g, a total pore volume of 2.5 cm³/g and average particle diameter of 35 μm was activated by calcining in dry air for 4 hours at 500° C. The activated silica was stored under argon. Dry impregnation in the absence of moisture was then carried out on 14 g of the silica using 43.9 g of the active phase prepared as described above.

The solid obtained, catalyst 1, contained 75.8% by weight of active phase.

Alkylation of isobutane by 2-butene using catalyst 1

Catalyst 1 was used to alkylate isobutane with 2-butene to produce branched paraffins with high octane numbers. 18 g of catalyst 1, as prepared above, was introduced into a Fischer & Porter reactor with a volume of 360 ml which had been purged with argon. The reactor containing the catalyst was closed, put under low vacuum, then cooled to a temperature of −20° C.

100 cm³ of isobutane was then added with stirring to the reactor containing the catalyst, the reactor being immersed in a cold bath at −6° C. The system (catalyst+isobutane) was stirred for 30 minutes to homogenize the temperature.

A mixture of isobutane and 2-butene containing 25% of 2-butene was continuously added for a total period of 8 hours. The temperature of the reactor was held at −5° C. for the whole injection period. The volume flow rate of the mixture (isobutane+2-butene) was 25 ml/h.

After reaction, the hydrocarbon phase was extracted from the reactor, then the isobutane was slowly evaporated off and the alkylate was recovered and analysed by gas chromatography. The composition by weight is given in Table 1. 100% of the olefin was converted.

Example 2

Preparation of comparative catalyst 2

23 g of freshly sublimed aluminum chloride and 20 ml of heptane were successively introduced into a glass flask provided with a magnetic stirrer, purged of air and moisture and held at 10° C., followed by portionwise introduction of 13.7 g of 1-butyl-3-methylimidazolium. A liquid composition was obtained.

16 g of silica with a specific surface area of 395 $m^2/g$, a total pore volume of 2.5 $cm^3/g$ and average particle diameter of 35 µm was activated by calcining in dry air for 4 hours at 500° C. The activated silica was stored under argon. Dry impregnation in the absence of moisture was then carried out on 14 g of the silica using 43.9 g of the active phase prepared using the method described above.

The solid obtained, catalyst 2, contained 75.8% by weight of active phase.

Catalyst 2 as prepared above was tested under the same operating conditions as those described for Example 1. The catalytic results obtained are given in Table 1. 100% of the olefin was converted.

TABLE 1

|  | CATALYST 1 (in accordance with invention) | CATALYST 2 (comparative) |
| --- | --- | --- |
| $C_5$–$C_7$ | 1.6 | 3.1 |
| $C_8$ total | 97.4 | 94.2 |
| $C_9^+$ | 1.0 | 2.7 |
| Chlorine content (ppm by weight) | 35 | 90 |

Table I demonstrates the effect of the presence of copper (I) in catalyst 1: under identical operating conditions, catalyst 1 had a higher selectivity for $C_8$ compounds and a lower selectivity for the undesirable heavy $C_9^+$ compounds. Further, catalyst 1 led to a smaller chlorine loss than catalyst 2.

Example 3

Preparation of catalyst 3, in accordance with the invention 15 g of silica with a total pore volume of 2.2 $cm^3/g$, a specific surface area of 420 $m^2/g$ and an average particle diameter of 60 µm was activated by calcining at 150° C. for 12 hours. The activated silica was stored under nitrogen. Dry impregnation was then carried out on 10 g of the silica using 27.4 g of the active phase prepared using the method described in Example 1.

The solid obtained, catalyst 3, contained 73.2% by weight of active phase. It was stored under argon in the absence of moisture. 15 g of catalyst 3, as prepared above, was introduced into a Fischer & Porter reactor with a volume of 360 ml which had been purged with argon. The reactor containing the catalyst was closed, put under low vacuum, then cooled to a temperature of −20° C.

150 $cm^3$ of isobutane was then added to the reactor containing the catalyst, with stirring (screw), the reactor being immersed in a cold bath at −5° C. The system (catalyst 3+isobutane) was stirred for 30 minutes to homogenize the temperature.

6.0 g per hour of 2-butene was steadily added for a total period of 6 hours. The temperature of the reactor was held at −5° C. for the whole injection period.

After reaction, the hydrocarbon phase was extracted from the reactor, then the isobutane was slowly evaporated off and the alkylate was recovered and analysed by gas chromatography. The composition by weight is given in Table 2. 100% of the olefin was converted.

Example 4

Preparation of comparative catalyst 4

15 g of dehydrated silica was prepared which was identical to that used in Example 3 using a method identical to the preparation of the catalyst in accordance with the invention described in Example 3. 10 g of the silica was then dry impregnated with 27.4 g of the active phase prepared as described in Example 2.

The solid obtained, catalyst 4, contained 73.2% by weight of the acid phase, it was stored under argon in the absence of moisture.

Alkylation of isobutane by 2-butene using catalyst 4

15 g of catalyst 4 as prepared above was introduced into a Fischer & Porter reactor with a volume of 360 ml which had been purged with argon. The reactor containing the catalyst was closed, put under low vacuum, then cooled to a temperature of −20° C.

150 $cm^3$ of isobutane was then added with stirring (screw) to the reactor containing the catalyst, the reactor being immersed in a cold bath at −5° C. The system (catalyst 4+isobutane) was stirred for 30 minutes to homogenize the temperature.

6.0 g of 2-butene per hour was steadily added for a total period of 6 hours. The temperature of the reactor was held at −5° C. for the whole injection period.

After reaction, the hydrocarbon phase was extracted from the reactor, the isobutane was slowly evaporated off and the alkylate was recovered and analysed by gas chromatography. The composition by weight is given in Table 2. 100% of the olefin was converted.

TABLE 2

|  | CATALYST 3 (in accordance with invention) | CATALYST 4 (comparative) |
| --- | --- | --- |
| $C_5$–$C_7$ | 3.3 | 4.1 |
| $C_8$ total | 92.1 | 88.3 |
| $C_9^+$ | 4.6 | 7.6 |
| Chlorine content (ppm by weight) | 30 | 110 |

Table 2 demonstrates the effect of the presence of copper (I) in catalyst 3: under identical operating conditions, catalyst 1 had a higher selectivity for $C_8$ compounds and a lower selectivity for the undesirable heavy $C_9^+$ compounds. Further, catalyst 3 led to a smaller chlorine loss than catalyst 4.

Example 5

15.3 g of catalyst 1 prepared as described in Example 1 was introduced into a steel reactor with a volume of 500 ml which had been purged with argon. The reactor containing the catalyst was closed and cooled to a temperature of −5° C.

The reactor containing catalyst 1 was then filled with isobutane which had been dried by passage over a molecular sieve. The reactor was cooled to −5° C. by circulating a cold liquid in the double envelope with which it was provided. The catalyst was taken up into suspension in the isobutane by starting up a mechanical stirring system. The moving part of the stirrer was a turbine with a rotational speed of 700 revolutions per minute. Stirring was maintained for 30 minutes to homogenize the temperature.

A mixture constituted by 4.9% by weight of 2-butene and 95.1% of isobutane was then injected into the reactor while stirring was continued, over a total period of 300 hours and at a flow rate of 63 g per hour. The temperature of the reactor was kept at −5° C. for the entire injection period. The stream leaving the reactor, composed of a mixture of alkylate and isobutane, was directly analysed without evaporation. Analysis was effected after 150 hours and 300 hours of operation. The results obtained, and the measured chlorine contents after evaporating off the isobutane, are shown in Table 3.

Example 6

15.3 g of catalyst 2 prepared as described in Example 2 was introduced into a steel reactor with a volume of 500 ml which had been purged with argon. The reactor containing the catalyst was closed and cooled to a temperature of −5° C.

A catalytic test was carried out under the same operating conditions as those used in Example 5. The analyses were effected after the same periods of injection of the feed. The results obtained, and the measured chlorine contents after evaporating off the isobutane, are shown in Table 3.

TABLE 3

|  | EXAMPLE 5 (catalyst 1 in accordance with invention) | | EXAMPLE 6 (Comparative catalyst 2) | |
| --- | --- | --- | --- | --- |
|  | t = 150 h | t = 300 h | t = 150 h | t = 300 h |
| $C_5$–$C_7$ | 0.7 | 0.7 | 2.2 | 5.5 |
| $C_8$ total | 98.7 | 98.5 | 93.3 | 87.6 |
| $C_9^+$ | 0.6 | 0.8 | 4.5 | 6.9 |
| Chlorine content (ppm by weight) | 45 | 52 | 115 | 195 |

Example 7

Preparation of catalyst 5, in accordance with the invention 40 g of silica with a specific surface area of 265 m²/g, a total pore volume of 0.25 cm³/g and an average particle diameter of 15 μm was activated by calcining in dry air for 4 hours at 500° C. The activated silica was stored under argon. Dry impregnation in the absence of moisture was then carried out on 30 g of the silica using 9.5 of the active phase prepared in Example 1.

The solid obtained, catalyst 5, contained 24% by weight of active phase.

Alkylation of isobutane by 2-butene using catalyst 5

Catalyst 5 was used to alkylate isobutane with 2-butene to produce branched paraffins with high octane numbers. 30 g of catalyst 5, as prepared above, was introduced into a Fischer & Porter reactor with a volume of 360 ml which had been purged with argon. The reactor containing the catalyst was closed, put under low vacuum, then cooled to a temperature of −20° C.

100 cm³ of isobutane was then added with stirring to the reactor containing the catalyst, the reactor being immersed in a cold bath at −5° C. The system (catalyst+isobutane) was stirred for 30 minutes to homogenize the temperature.

A mixture of isobutane and 2-butene containing 25% of 2-butene was continuously added for a total period of 6 hours. The temperature of the reactor was held at −5° C. for the whole injection period. The volume flow rate of the mixture (isobutane+2-butene) was 20 ml/h.

After reaction, the hydrocarbon phase was extracted from the reactor, then the isobutane was slowly evaporated off and the alkylate was recovered and analysed by gas chromatography. The composition by weight is given in Table 4. 100% of the olefin was converted.

Example 8

Preparation of comparative catalyst 6

40 g of silica with a specific surface area of 265 m²/g, a total pore volume of 0.25 ml/g and an average particle diameter of 15 μm was activated by calcining in dry air for 4 hours at 500° C. The activated silica was stored under argon. Dry impregnation in the absence of moisture was then carried out on 30 g of the silica using 9.5 g of the active phase prepared in Example 2.

The solid obtained, catalyst 6, contained 24% by weight of active phase.

Catalyst 6 as prepared above was tested under the same operating conditions as those described for Example 1. The catalytic results obtained are given in Table 4. 100% of the olefin was converted.

TABLE 4

|  | CATALYST 5 (in accordance with invention) | CATALYST 6 (comparative) |
| --- | --- | --- |
| $C_5$–$C_7$ | 2.0 | 3.1 |
| $C_8$ total | 96.2 | 93.5 |
| $C_9^+$ | 1.8 | 3.4 |
| Chlorine content (ppm by weight) | 30 | 80 |

Table 4 demonstrates the effect of the presence of copper (I) in catalyst 5: under identical operating conditions, catalyst 1 had a higher selectivity for $C_8$ compounds and a lower selectivity for the undesirable heavy $C_9^+$ compounds. Further, catalyst 5 led to a smaller chlorine loss than catalyst 6.

We claim:

1. A catalyst containing a porous organic or mineral support and at least one active phase-comprising (a) at least one aluminum halide, (b) at least one compound selected from the group consisting of quaternary ammonium halides and amine hydrohalides, and (c) at least one cuprous compound, the support having been impregnated with the active phase, the catalyst having a particle size of an average diameter in the range of 0.1 μm to 150 μm, and the support, before being impregnated with the active phase, having a total pore volume in the range of 0.1 cm³/g to 6 cm³/g.

2. A catalyst according to claim 1, in which the cuprous compound is selected from the group consisting of cuprous halides, cuprous acetate, cuprous sulphate, cuprous nitrate and cuprous perchlorate.

3. A catalyst according to claim 1, in which the cuprous compound is a cuprous halide.

4. A catalyst according to claim 1, in which the cuprous compound is selected from the group consisting of copper (I) chloride and copper (I) bromide.

5. A catalyst according to claim 1, in which the aluminum halide is selected from the group consisting of aluminum chloride and aluminum bromide.

6. A catalyst according to claim 1, in which the quaternary ammonium halide is selected from the group consisting of compounds with general formula:

   (I)

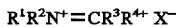   (II)

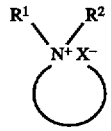   (III)

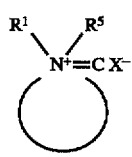   (IV)

where $R^1$, $R^2$, $R^3$, $R^4$ and $R^5$, which may be identical or different, each represent hydrocarbon residues containing 1 to 12 carbon atoms, where $R^5$ can also represent hydrogen, and in which the cyclic part is constituted by 4 to 10 atoms, and in which X represents a halide ion.

7. A catalyst according to claim 1, in which the quaternary ammonium halide has general formula:

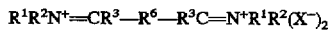

where $R^1$, $R^2$ and $R^3$, which may be identical or different, represent hydrocarbon residues containing 1 to 12 carbon atoms, and $R^6$ represents an alkylene or phenylene residue, and in which X represents a halide ion.

8. A catalyst according to claim 1, in which the quaternary ammonium halide is selected from the group consisting of N-butylpyridinium chloride, ethylpyridinium bromide, 1-butyl-3-methylimidazolium chloride, diethylpyrazolium chloride, and 1-ethyl-3-methyl-imidazolium chloride.

9. A catalyst according to claim 1, in which the amine hydrohalide is selected from the group consisting of hydrohalides containing one mole of hydrohalic acid per mole of amine and hydrohalides containing 2 moles of hydrohalic acid per mole of amine.

10. A catalyst according to claim 9, in which the amine is selected from the group of compounds with general formulae:

   (I)

   (II)

   (III)

   (IV)

where $R'^1$, $R'^2$ and $R'^3$, which may be identical or different, represent hydrocarbon residues containing 1 to 12 carbon atoms, and in which the cyclic part is constituted by 4 to 10 atoms, one of the substituents $R'^1$, $R'^2$, or $R'^3$ optionally being hydrogen.

11. A catalyst according to claim 9, in which the hydrohalic acid is selected from the group consisting of hydrochloric acid and hydrobromic acid.

12. A catalyst according to claim 1, in which the amine hydrohalide is selected from the group consisting of pyridine hydrochlorides and hydrobromides, 2-, 3- and 4-picolines, N-methylimidazole, N-butylimidazole, lutidines, 2-ethylpyridine, 3-isopropylpyridine, 2- or 4-chloropyridine, N,N-dimethyl-4-aminopyridine, piperidine, and N-methylimidazoline.

13. A catalyst according to claim 1, in which the molar ratio between (a) the aluminum halide and (b) the quaternary ammonium halide and amine hydrohalide is in the range 1.1:1 to 3.5:1.

14. A catalyst according to claim 1, in which the molar ratio between the aluminum halide and the cuprous halide is in the range 1:0.1 to 1:1.

15. A process comprising catalytically alkylating at least one isoparaffin selected from the group consisting of isobutane and isopentane with at least one olefin containing 2 to 6 carbon atoms, at a reaction temperature in the range of −20° C. to +25° C., at a pressure in the reaction zone sufficient to maintain the hydrocarbons in the liquid state in said zone, and wherein the alkylating is conducted in contact with the catalyst of claim 1.

16. A catalyst according to claim 1, in which the support is silica.

17. A process according to claim 16, in which the catalyst is employed in a near perfectly mixed reaction zone.

18. A process according to claim 16, in which the catalyst is employed in a co-current mobile bed.

* * * * *